United States Patent
Yan et al.

(10) Patent No.: US 12,258,550 B2
(45) Date of Patent: Mar. 25, 2025

(54) APPARATUS FOR ENRICHING AND SCREENING TARGET OBJECT SUCH AS CELL, BACTERIA OR BIOMOLECULE FROM SAMPLE

(71) Applicant: HEMOSMART MEDICAL TECHNOLOGY LTD., Kunshan (CN)

(72) Inventors: Jing Yan, Zhangjiagang (CN); Charmet Jerome, West Midlands (GB); Ziyi Yu, Zhangjiagang (CN); Weiwei Ma, Zhangjiagang (CN); Jie Wang, Zhangjiagang (CN); Bauer Wolfgang-Andreas Christian, Zhangjiagang (CN)

(73) Assignee: HEMOSMART MEDICAL TECHNOLOGY LTD., Kunshan (CN)

( * ) Notice: Subject to any disclaimer, the term of this patent is extended or adjusted under 35 U.S.C. 154(b) by 960 days.

(21) Appl. No.: 17/058,665

(22) PCT Filed: Oct. 10, 2018

(86) PCT No.: PCT/CN2018/109692
§ 371 (c)(1),
(2) Date: Nov. 25, 2020

(87) PCT Pub. No.: WO2019/223214
PCT Pub. Date: Nov. 28, 2019

(65) Prior Publication Data
US 2021/0198612 A1    Jul. 1, 2021

(30) Foreign Application Priority Data
May 25, 2018    (CN) .......................... 201810513620.3

(51) Int. Cl.
C12M 1/34    (2006.01)
C12M 1/32    (2006.01)

(52) U.S. Cl.
CPC ............ *C12M 41/36* (2013.01); *C12M 23/12* (2013.01)

(58) Field of Classification Search
None
See application file for complete search history.

(56) References Cited

U.S. PATENT DOCUMENTS 2,677,646 A * 5/1954 Lovell .................... C12M 23/38
                                                          435/288.3
4,335,206 A * 6/1982 Wilkins ................... C12Q 1/04
                                                          435/39

(Continued)

FOREIGN PATENT DOCUMENTS

CN    1560223 A    1/2005
CN    107338184 A    11/2017

(Continued)

*Primary Examiner* — Brian R Gordon
(74) *Attorney, Agent, or Firm* — Schmeiser, Olsen & Watts LLP

(57) ABSTRACT

Disclosed is an apparatus for enriching and screening a target object such as a cell, bacteria or biomolecule from a sample. The apparatus includes a plurality of multi-channel mesh bodies arranged in parallel, and each multi-channel mesh body includes a mesh body formed by intersecting a plurality of threads, a plurality of screen pores formed by intersecting the plurality of threads, and a capturing layer formed on the mesh body. The capturing layer includes a capturing material specifically binding with the target object.

6 Claims, 5 Drawing Sheets

(56) References Cited

U.S. PATENT DOCUMENTS

| | | | | |
|---|---|---|---|---|
| 4,578,168 | A * | 3/1986 | Hofmann | C12N 13/00 204/272 |
| 6,368,592 | B1 * | 4/2002 | Colton | C12M 23/08 435/325 |
| 6,844,187 | B1 * | 1/2005 | Wechsler | C12M 29/04 435/395 |
| 11,453,849 | B1 * | 9/2022 | Poon | C11D 3/1246 |
| 11,951,422 | B2 * | 4/2024 | Yokota | C12M 33/14 |
| 2004/0158226 | A1 * | 8/2004 | Soo Hoo | C12M 23/34 435/293.1 |
| 2009/0111193 | A1 * | 4/2009 | Cooney | G01N 1/405 436/178 |
| 2010/0203638 | A1 * | 8/2010 | Adachi | C12M 21/08 435/395 |
| 2011/0233148 | A1 * | 9/2011 | Antonchuk | B01D 35/30 210/477 |
| 2011/0244554 | A1 * | 10/2011 | Alsop | C09K 8/582 435/283.1 |
| 2011/0318814 | A1 * | 12/2011 | Kshirsagar | G01N 1/405 435/257.1 |
| 2012/0237963 | A1 * | 9/2012 | Lange | C12M 41/34 435/29 |
| 2013/0087643 | A1 * | 4/2013 | Tremolada | A61M 1/892 241/24.1 |
| 2014/0073063 | A1 * | 3/2014 | Lieber | A61L 27/025 438/1 |
| 2016/0041075 | A1 * | 2/2016 | Kamba | G01N 1/4077 422/534 |
| 2017/0368226 | A1 * | 12/2017 | Pilkington | A61M 5/31513 |
| 2018/0362917 | A1 * | 12/2018 | Kondo | B01D 39/10 |
| 2019/0112565 | A1 * | 4/2019 | Kagawa | C12N 5/0644 |
| 2020/0061258 | A1 * | 2/2020 | Khalaj | B26D 3/185 |
| 2020/0139303 | A1 * | 5/2020 | Dupont | B01D 63/082 |
| 2021/0077925 | A1 * | 3/2021 | Yokota | B01D 29/35 |
| 2021/0180116 | A1 * | 6/2021 | Hoffmann | C12Q 1/6806 |
| 2021/0403850 | A1 * | 12/2021 | Takezawa | B01D 63/087 |
| 2022/0041971 | A1 * | 2/2022 | Hatanaka | C12M 25/16 |

FOREIGN PATENT DOCUMENTS

| | | |
|---|---|---|
| CN | 107338185 A | 11/2017 |
| CN | 207276608 U | 4/2018 |
| CN | 207276609 U | 4/2018 |
| CN | 208362321 U | 1/2019 |

* cited by examiner

APPARATUS FOR ENRICHING AND SCREENING TARGET OBJECT SUCH AS CELL, BACTERIA OR BIOMOLECULE FROM SAMPLE

TECHNICAL FIELD

The present disclosure relates to an apparatus for enriching and screening a target object such as a cell, bacteria or biomolecule from a sample.

BACKGROUND

In the detection of blood and biological samples, rare cells and rare molecules in the detection samples are often detected, the successful separation and enrichment of these rare target objects or molecules is the key to the accuracy of the detection. For example, in human production and life, human body fluids, food, and detection objects in the natural environment need to be detected, for example, in medical practice, food safety, and environmental monitoring, it often needs to detect cells (such as circulating tumor cells, nucleated red blood cells), and microorganisms (for example, in medical treatment human body fluids are detected for *Streptococcus pneumoniae, legionella*, fungi and special pathogens such as *mycoplasma, chlamydia, rickettsia*, spirochetes, viruses, etc.); in the field of food safety, microorganisms are detected, such as coliforms, pathogenic bacteria (including *Salmonella, Shigella, Staphylococcus aureus*, pathogenic *Streptococcus*, etc.), molds and mycotoxins (for example, *Aspergillus flavus* and *Aspergillus parasiticus, Penicillium citrinum* and *Penicillium islandicum, Fusarium moniliforme* and *Fusarium graminearum*, etc.), other microorganisms in food safety also include viruses (for example, hepatitis virus, swine fever virus, chicken Newcastle disease virus, Marek's virus, foot-and-mouth disease virus, rabies virus, swine vesicular disease virus, etc.), and in addition, in food safety inspection, parasites are also listed by many scholars as indicators of microbiological examination (for example, *Trichinella spiralis, Cysticercus cellulosae*). In addition to this, certain proteins, nucleic acids, etc. are also used as detection objects, such as common early diagnosis marker screening and genetic diagnosis in clinical practice. Different detection methods and detection platforms need to be applied to different detection objects, and due to the low concentration of some detection objects, this puts high demands on the detection methods.

Taking the detection of nucleated red blood cells as an example, nucleated red blood cells cannot be seen in the peripheral blood of normal adults, and a small amount of nucleated red blood cells can be seen in the peripheral blood of newborns within 1 week of birth. Nucleated red blood cells in adult peripheral blood are pathological phenomena, and nucleated red blood cells are related to proliferative anemia, erythremic myelosis, extramedullary hematopoiesis, and others such as metastatic cancer of bone marrow and severe hypoxia. In the detection projects in production and life, a high-sensitivity, low-cost, and rapid detection method and platform is required.

Taking the detection of circulating tumor cells as an example, circulating tumor cells, namely tumor cells in the blood circulation, are considered to be related to the distant metastasis of tumors. Generally, there are only 1-10 circulating tumor cells in 10 mL of blood of cancer patients, and its slow capture speed or poor specificity is an urgent problem that needs to be solved for rapid detection of patient blood samples. For the detection of circulating tumor cells, a high-sensitivity, high-accuracy, and rapid detection method and detection platform is required.

The present disclosure aims at the enrichment of cells, bacteria, or target molecules in biological samples, and adopts microfluidic enrichment mechanism technology, which can perform rapid detection on different types of detection objects such as cells, proteins, nucleic acids, and microorganisms (including viruses and bacteria), and which will be described in detail below.

Another disclosure CN 107338184 A similar to the present disclosure discloses a multi-channel mesh body and a device for capturing biomolecules in cells or solutions, and the device comprises at least one or a plurality of stacked multi-channel mesh body, a capturing device comprises a main body having an inlet, a first outlet, and a cavity located between the inlet and the first outlet, an enriching and screening mechanism is fixed in the cavity, and the inlet is in communication with the first outlet and the cavity. The multi-channel mesh body comprises a mesh body and a capturing layer formed on the mesh body, and the capturing layer comprises a capturing material that can specifically bind with target cells, bacteria, or biomolecules. The multi-channel mesh body and device in this patent have high specificity and high flux, and are suitable for capturing cells or biomolecules in a solution by molecules expressed by cells, and are particularly suitable for capturing and sorting circulating tumor cells. However, because the multi-channel mesh body in this patent is only one layer or stacked multilayer, and when it is stacked multilayer, there is no angle between multi layers of multi-channel mesh bodies, that is, the screen pores of the multi layers of multi-channel mesh bodies are overlapped, therefore, when circulating tumor cells are not captured during passing through the first layer of multi-channel mesh body, the uncaptured circulating tumor cells will pass directly through the remaining multi-channel mesh bodies without being captured due to the contact area between the cells and the remaining multi-channel mesh bodies through which they passes later is relatively small, resulting in a low capture rate of the device of this patent. The present disclosure chooses to use a plurality of layers of screens and a variety of capturing materials, which can be used for various detection objects of the above-mentioned different types, therefore, the present disclosure is obviously different from the above-mentioned patent and has original innovation.

SUMMARY

An aspect of the disclosure provides an apparatus for enriching and screening a target object such as a cell, bacteria, or biomolecule from a sample with a high capture efficient.

An aspect relates to an apparatus for enriching and screening a target object such as a cell, bacteria or biomolecule from a sample (herein also referred as an enriching and screening mechanism), comprises a plurality of multi-channel mesh bodies arranged in parallel, each multi-channel mesh body comprises a mesh body formed by intersecting a plurality of mesh wires, a plurality of screen pores formed by intersecting the plurality of mesh wires, and a capturing layer formed on the mesh body, the capturing layer comprises a capturing material that can specifically binding with the target object, and the screen pores of two adjacent layers of the multi-channel mesh bodies are partially staggered.

In an embodiment, the plurality of multi-channel mesh bodies is arranged along a direction perpendicular to planes in which the mesh bodies are located. For instance, when the planes in which the multi-channel mesh bodies are located are horizontal planes, the plurality of multi-channel mesh bodies is arranged along a vertical direction.

Herein, "the screen pores of two adjacent layers of the multi-channel mesh bodies are partially staggered" means that the screen pores of one layer of the multi-channel mesh bodies is partially covered by the mesh wires of another layer of the multi-channel mesh bodies, that is to say, viewing from the top view of this device, the plurality of multi-channel mesh bodies does not coincide completely.

In an embodiment, in the two adjacent layers of multi-channel mesh bodies, a lower layer of multi-channel mesh body is rotated 5 to 180°, preferably 5 to 179° with respect to an upper layer of multi-channel mesh body. More preferably, in the two adjacent layers of the multi-channel mesh bodies, the lower layer of multi-channel mesh body is rotated 10 to 90° with respect to the upper layer of multi-channel mesh body. Further preferably, in the two adjacent layers of the multi-channel mesh bodies, the lower layer of multi-channel mesh body is rotated 30 to 60° with respect to the upper layer of multi-channel mesh body.

In an embodiment, each layer of multi-channel mesh bodies is rotated in the same direction with respect to its upper layer.

Herein, "rotated in the same direction" means that each layer of the multi-channel mesh bodies is rotated clockwise or counterclockwise with respect to its upper layer. When an (N+1)th layer of the multi-channel mesh bodies is rotated clockwise with respect to an Nth layer of the multi-channel mesh bodies, all layers of the multi-channel mesh bodies in the capturing device are rotated clockwise with respect to their upper layers of the multi-channel mesh bodies; when the (N+1)th layer of the multi-channel mesh bodies is rotated counterclockwise with respect to the Nth layer of the multi-channel mesh bodies, all layers of the multi-channel mesh bodies in the capturing device are rotated counterclockwise with respect to their upper layers of the multi-channel mesh bodies, the above-mentioned Nth represents the number of layers of the multi-channel mesh bodies.

In an embodiment, each layer of the multi-channel mesh bodies is rotated at the same angle with respect to its upper layer.

Herein, "a rotation angle" refers to that the angle at which a layer of the multi-channel mesh bodies is rotated clockwise or counterclockwise with respect to its upper layer, taking the center of the layer of the multi-channel mesh bodies as the center of rotation, with the normal direction of the rotation plane perpendicular to the plane of the layer of the multi-channel mesh bodies. "Rotated at the same angle" refers to that the rotation angle of an (N+2)th layer of the multi-channel mesh bodies with respect to an (N+1)th layer of the multi-channel mesh bodies is the same as the rotation angle of an (N+1)th layer of the multi-channel mesh bodies with respect to an Nth layer of the multi-channel mesh bodies, wherein Nth represents the current layer of the multi-channel mesh bodies.

Herein, "a diameter of the mesh wire" refers to the width of the mesh wire in the top view of the multi-channel mesh bodies. The diameter of the mesh wire generally ranges from 10 μm to 500 μm, preferably 20 μm to 200 μm, further preferably 20 to 50 μm. In a specific embodiment, the diameter of the mesh wire ranges from 40 to 50 μm.

Herein, "a thickness of the mesh wire" refers to a distance between the upper and lower surfaces of a multi-channel mesh body. The thickness of the mesh wire generally ranges from 10 μm to 500 μm, preferably 20 μm to 200 μm, further preferably 20 to 50 μm. In a specific embodiment, the thickness of the mesh wire ranges from 40 to 50 μm.

In an embodiment, the cross-sectional area of the screen pores generally ranges from 10 to 6000 $\mu m^2$, preferably 20 to 3000 $\mu m^2$, further preferably 700 to 3000 $\mu m^2$, more preferably 700 to 2000 $\mu m^2$, and more further preferably 700 to 1000 $\mu m^2$ in some embodiments.

Herein, "a gap between two adjacent layers of the multi-channel mesh bodies" refers to a distance from the lower surface of the upper layer of multi-channel mesh body to the upper surface of the lower layer of multi-channel mesh body. The gap between two adjacent layers of the multi-channel mesh bodies generally ranges from 0.1 to 10 mm, preferably 0.5 to 3 mm, more preferably 0.5 to 1.5 mm.

In an embodiment, the number of the multi-channel mesh bodies can range from 2 to 30, preferably 3 to 15, more preferably 5 to 10.

In an embodiment, the number of the multi-channel mesh bodies ranges from 5 to 12, the mesh wires have a diameter of 20 μm to 50 μm and a thickness of 20 μm to 50 μm, the cross-sectional area of the screen pores ranges from 700 to 3000 $\mu m^2$, and the gap between two adjacent layers of the multi-channel mesh bodies ranges from 0.5 to 3 mm.

In an embodiment, the shape of the cross section of the the screen pores is not particularly limited, and may be selected from square, rectangular, triangular, polygonal, circular, parallelogram, trapezoid, and combinations thereof, wherein square is preferred.

Herein, polygon is a closed figure formed by five or more sides.

In an embodiment, the capturing materials on at least two layers of the multi-channel mesh bodies are different. Further preferably, the capturing materials on at least three layers of the multi-channel mesh bodies are different. More preferably, in the enriching and screening mechanism, the capturing materials on at least four layers of the multi-channel mesh bodies are different. Most preferably, the capturing materials on each layer of the multi-channel mesh bodies are different.

In an embodiment, in the enriching and screening mechanism, the capturing materials on at least two layers of the multi-channel mesh bodies specifically bind with the same kind of target object, thus the specificity of the enriching and screening mechanism is increased, false negatives and false positives are reduced, and the capture rate of the target object is further improved.

In an embodiment, the capturing materials on at least three layers of the multi-channel mesh bodies specifically bind with the same kind of target object; more further preferably, the capturing materials on at least four layers of the multi-channel mesh bodies specifically bind with the same kind of target object; most preferably, the capturing material on each layer of the multi-channel mesh bodies specifically binds with the same kind of target object.

In an embodiment, in the plurality of multi-channel mesh bodies, the capturing material on at least one layer of multi-channel mesh body specifically binds with a kind of target object, the capturing material on at least another one layer of multi-channel mesh body specifically binds with another kind of target object, thus after the screening finishes, the target objects on the respective multi-channel mesh bodies can be separated after the respective multi-channel mesh bodies are detached, and thus screening multiple target objects at one time is achieved, and the working efficiency and application range are improved.

In an embodiment, the target objects on at least three layers of the multi-channel mesh bodies are respectively aimed at three different target objects. In an embodiment, the target objects on at least four layers of the multi-channel mesh bodies are respectively aimed at four different target objects. In an embodiment, the target objects on at least five layers of the multi-channel mesh bodies are respectively aimed at five different target objects. In an embodiment, the target object on each layer of the multi-channel mesh bodies specifically binds with different target objects.

In an embodiment, the target objects can be conventional targets that need to be separated and detected, and are not particularly limited. Generally, the target object comprises, but is not limited to, cells, bacteria, and biomolecules, and may be selected from cells, bacteria, biomolecules, and combinations thereof. Correspondingly, the capturing material is a specific recognition molecule for the target object, such as antibodies, phages, nucleic acid aptamers and the like. The target object specifically is, for example EpCAM (epithelial cell adhesion molecule), EphB4, EGFR, HER2, HER-2/neu, MUC-1, folate receptor, AFP, CEA, Cyfra21-1, TPA, TPS, NMP22, β2-MG, thyroglobulin, ferritin, CA19-9, CA125, CA50, CA72-4, CA242, CA15-3, SCC, LDH, NSE, PSA, ER, progesterone receptor, HCG β-hCG, prolactin, ACTH, calcitonin, DHEA-S, cortisol, aldosterone, uPA/PAI-1,5-hydroxytryptamine, 5-hydroxyindole acetic acid, HGH, FSH, LH, TSH, paraprotein, thymidine kinase, neopterin, SEA, protein S-100, M2-PK, chromogranin A, bone-specific alkaline phosphatase, deoxypyridinoline, CASA, epinephrine substances, catecholamines, homovanillic acid, epinephrine substances, vanillylmandelic acid, f-PSA, PCA3, AFP, placental alkaline phosphatase, calcitonin, gastrin, TSA, AFU, γGT, ALP, CA549, PAP, Bence-Jones protein, and various bacteria and other types of target objects.

In an embodiment, the capturing material is bonded to the mesh bodies by means of physical adsorption and/or chemical bonding.

In an embodiment, the capturing material is connected to the mesh bodies through Traut's reagent or a thiolate molecule with biotin-avidin.

In an embodiment, the enriching and screening mechanism of the present disclosure further comprises a main body with an inlet, a first outlet, and a cavity between the inlet and the first outlet, the plurality of multi-channel mesh bodies is fixed within the cavity, and the inlet and the first outlet are communicated with the cavity. The main body is preferably manufactured using the existing manufacturing technology, such as injection molding technology. The material of the main body should be compatible with solvents, for example, PEEK.

In an embodiment, the cavity is partitioned into two parts, namely a first cavity and a second cavity by the plurality of multi-channel mesh bodies.

In an embodiment, the plurality of multi-channel mesh bodies is arranged horizontally, the inlet is located above the enriching and screening mechanism and communicated with the first cavity, and the first outlet is located below the enriching and screening mechanism and communicated with the second cavity.

In an embodiment, center lines of the inlet and the first outlet are perpendicular to the plane in which the multi-channel mesh bodies are located.

In an embodiment, the main body further has a second outlet, and the main body is provided with a microfluidic passage communicated with the cavity and the second outlet for collecting the captured cells, bacteria, or biomolecules.

In an embodiment, the enriching and screening mechanism further comprises a counting mechanism arranged within the microfluidic passage for counting the captured cells, bacterial, or biomolecules.

In an embodiment, the counting mechanism comprises an impedance measuring electrode.

Due to the implementation of the above technical solutions, the present disclosure has the following advantages over the prior art:

By partially staggering screen pores of two adjacent layers of multi-channel mesh bodies, the present disclosure increases the probability of target cells, bacteria or biomolecules contacting the multi-channel mesh body under the condition of ensuring higher flux, thereby improving the capture rate of the multi-channel mesh bodies to the target object.

Wherein, 11—inlet; 12—first outlet; 20—multi-channel mesh body; 20a—first mesh; 20b—second mesh; 21—capturing material; 22—screen pore; 23—mesh wire; 231—first mesh wire; 232—second mesh wire; 3—target object.

DETAILED DESCRIPTION OF EXEMPLARY EMBODIMENTS

For more clearly explaining the technical solutions of the present disclosure, the present disclosure is described in detail combining with the accompanying drawings and embodiments in the following. Apparently, the below described embodiments and drawings are merely a part of the non-restrictive embodiments of the present disclosure, not all the embodiments. Based on the embodiments of the present disclosure, all other embodiments obtained by one of ordinary skill in the art without creative work belong to the protective scope of the present disclosure.

In a specific embodiment of the present disclosure, the enriching and screening apparatus comprises a main body, a cavity, a counting mechanism, and a plurality of multi-channel mesh bodies 20. The main body comprises an inlet 11, a first outlet 12, a second outlet, and a microfluidic passage. The main body is preferably manufactured using the existing manufacturing technology, such as injection molding technology. The material of the main body should be compatible with solvents, for example, PEEK. The microfluidic passage is communicated with the cavity and the second outlet for collecting the captured target object 3 (which may be cells, bacteria, or biomolecules, etc.).

Figure 1:
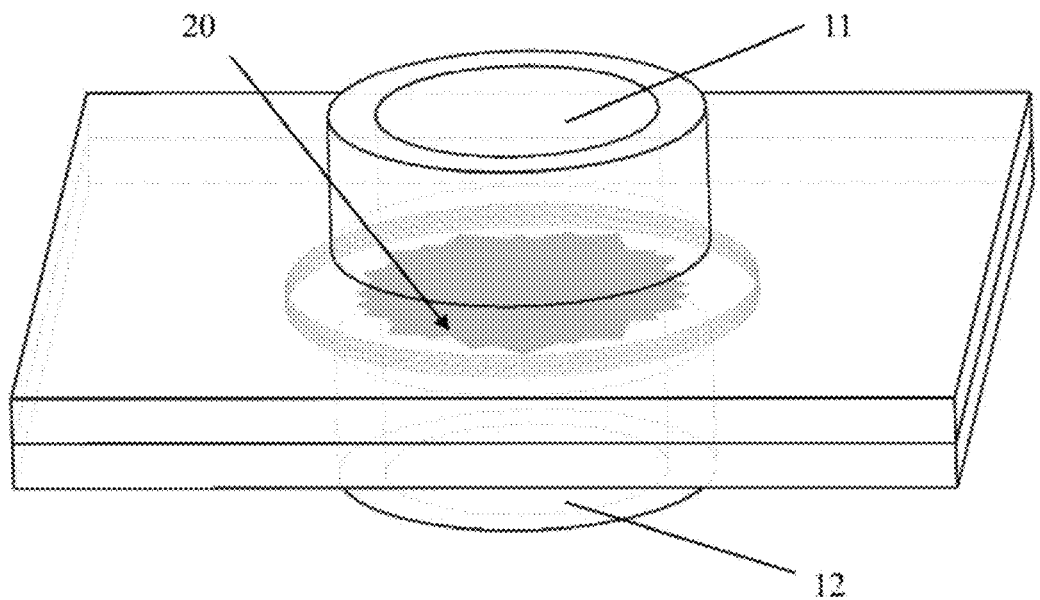
FIG. 1 is a schematic structure diagram of an enriching and screening mechanism of an embodiment.

As shown in FIG. 1, the inlet 11 is located above the plurality of multi-channel mesh bodies, and the first outlet 12 is located below the plurality of multi-channel mesh bodies. Preferably, the center lines of the inlet 11 and the first outlet 12 are perpendicular to the plane in which the multi-channel mesh bodies 20 are located. The cavity is located between the inlet 11 and the first outlet 12, and the plurality of multi-channel mesh bodies 20 is fixed within the cavity, and the inlet 11 and the first outlet 12 are communicated with the cavity. The cavity is partitioned into two parts, namely a first cavity and a second cavity by the plurality of multi-channel mesh bodies 20. The inlet 11 is communicated with the first cavity, and the first outlet 12 is communicated with the second cavity.

The counting mechanism is arranged within the microfluidic passage and used to count the captured target object 3. Preferably, the counting mechanism comprises an impedance measuring electrode.

Figure 2:
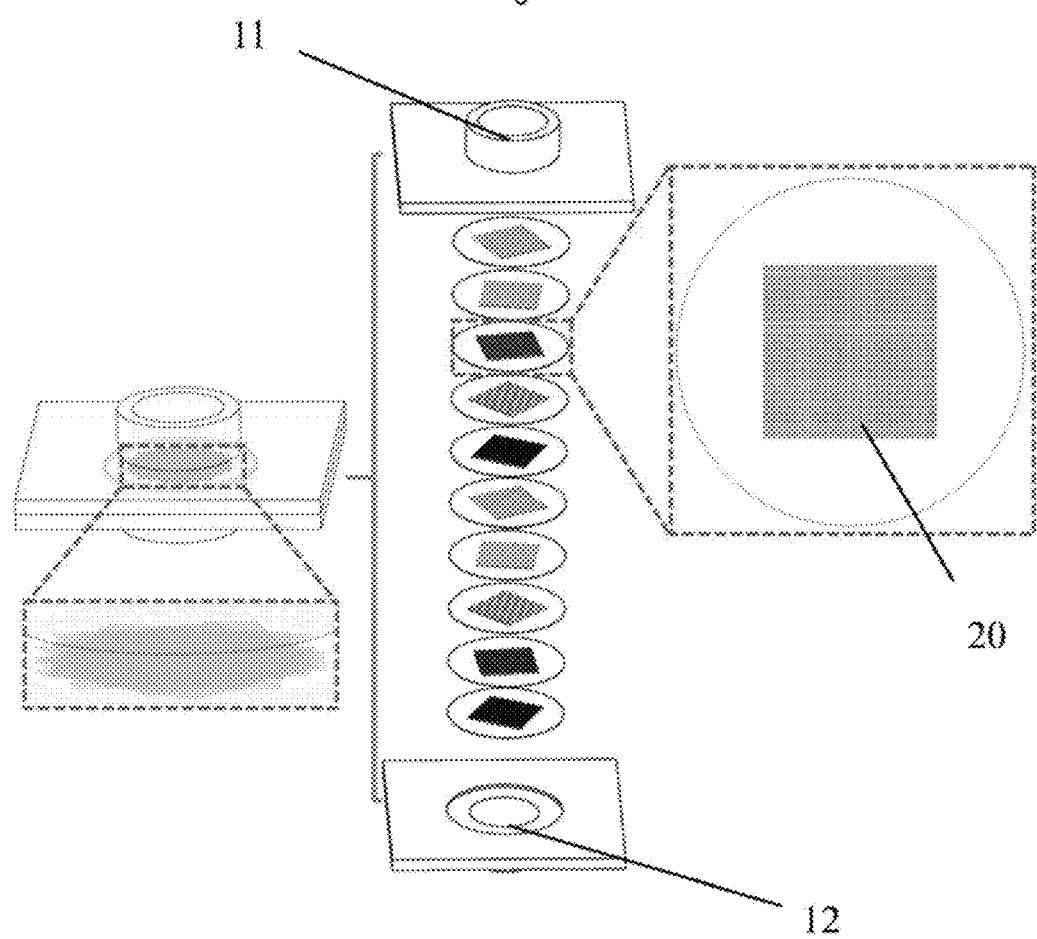
FIG. 2 is an explosive view of the enriching and screening mechanism of an embodiment.
Figure 5:
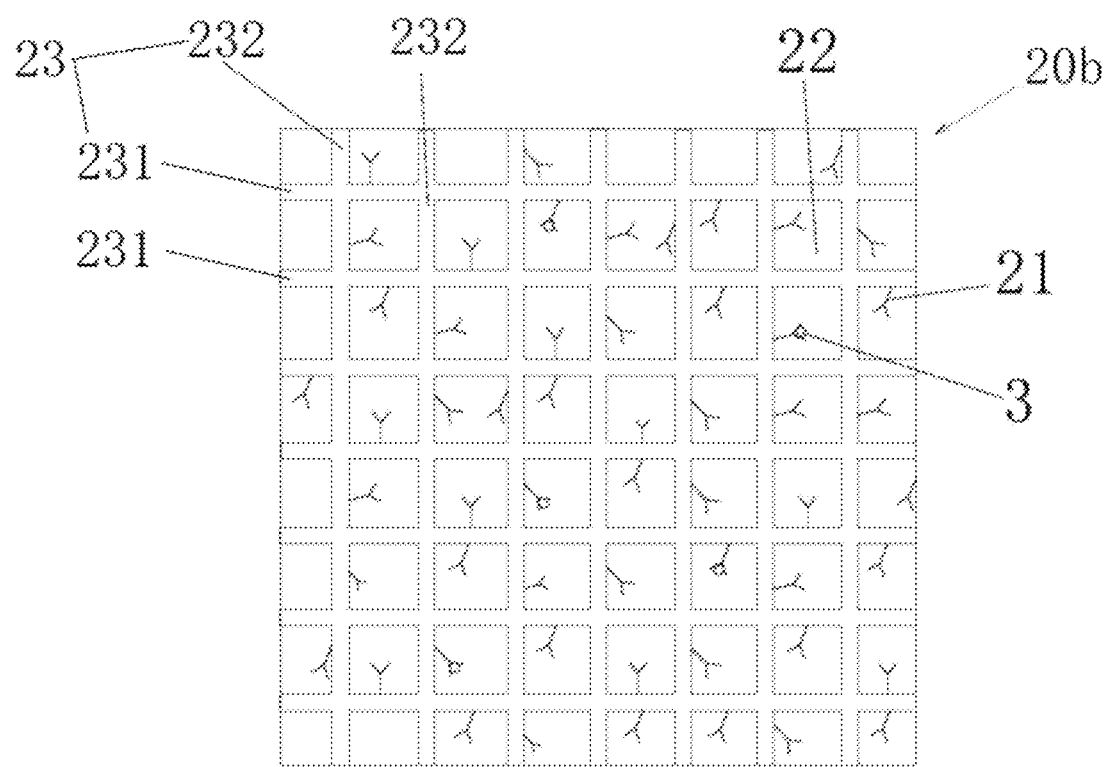
FIG. 5 is a top view of a multi-channel mesh body with captured target objects.
Figure 6:
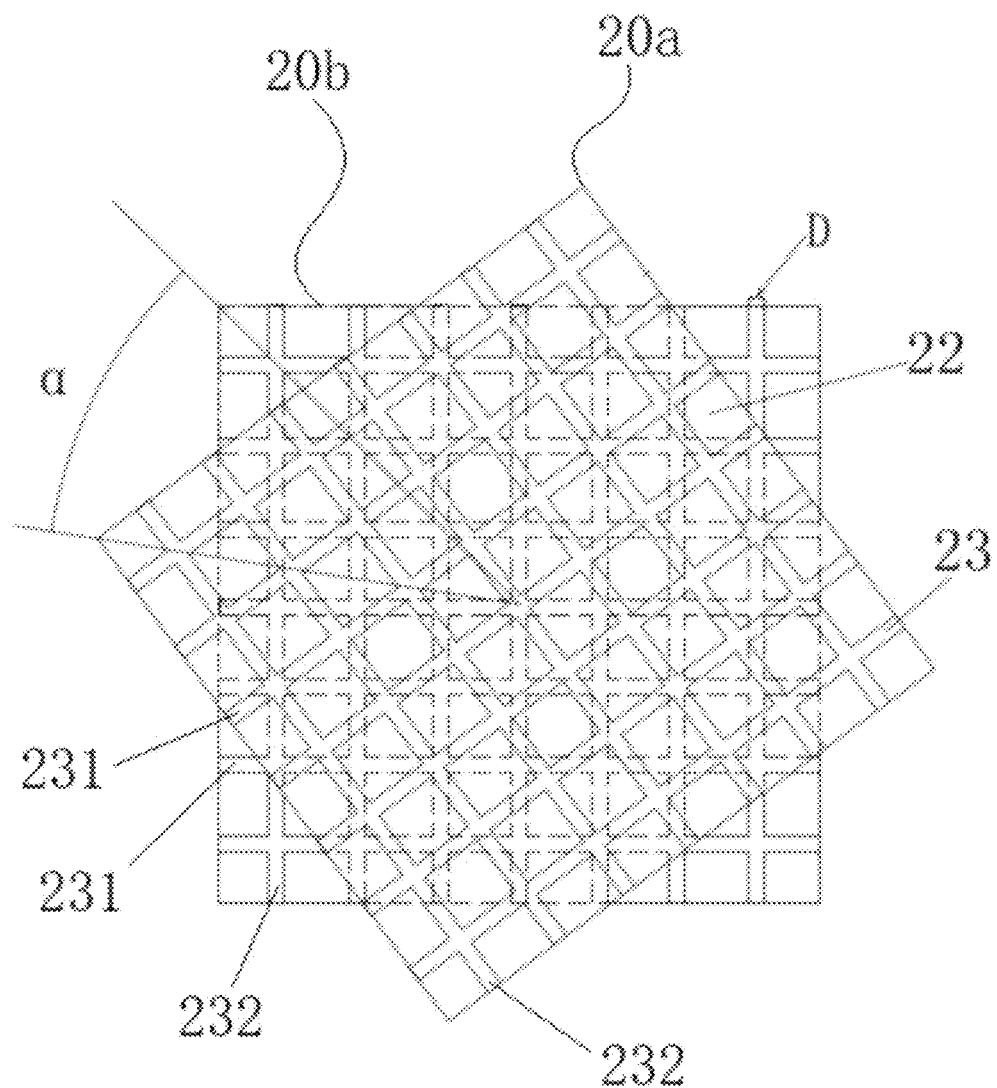
FIG. 6 is a top view of multi-channel mesh bodies with screen pores partially staggered.

As shown in FIG. 2, the plurality of multi-channel mesh bodies are arranged in parallel. Herein, the number of the multi-channel mesh bodies 20 is 2 to 30, preferably 5 to 10. As shown in FIGS. 5 and 6, each multi-channel mesh body 20, such as a first mesh 20a or a second mesh 20b comprises a mesh body formed by intersecting a plurality of mesh wires 23, the mesh wires 23 includes a plurality of first mesh wires 231 arranged in parallel and a plurality of second mesh wires 232 arranged in parallel, a plurality of screen pores 22 are formed by intersecting the plurality of the first mesh wires 231 and the second mesh wires 232, and a capturing layer is formed on the mesh body.

In order to specifically bind with the target object (cells, bacteria, or biomolecules, etc.) 3, the capturing layer comprises capturing material 21 that can specifically bind with the target object 3. In particular, the capturing material 21 is bonded to the mesh bodies by means of physical adsorption and/or chemical bonding. Preferably, the capturing material 21 is connected to the mesh bodies through Traut's reagent or a thiolate molecule with biotin-avidin.

In a specific embodiment, the target object 3 is circulating tumor cells (CTCs), hereinafter referred to as CTCs. In another specific embodiment, the target object 3 is *Escherichia coli*.

The probability of target object 3 contacting the multi-channel mesh bodies 20 is increased in order to ensure the high flux and while improve the capture rate. The screen pores of two adjacent layers of multi-channel mesh bodies 20 are partially staggered.

Figure 3:
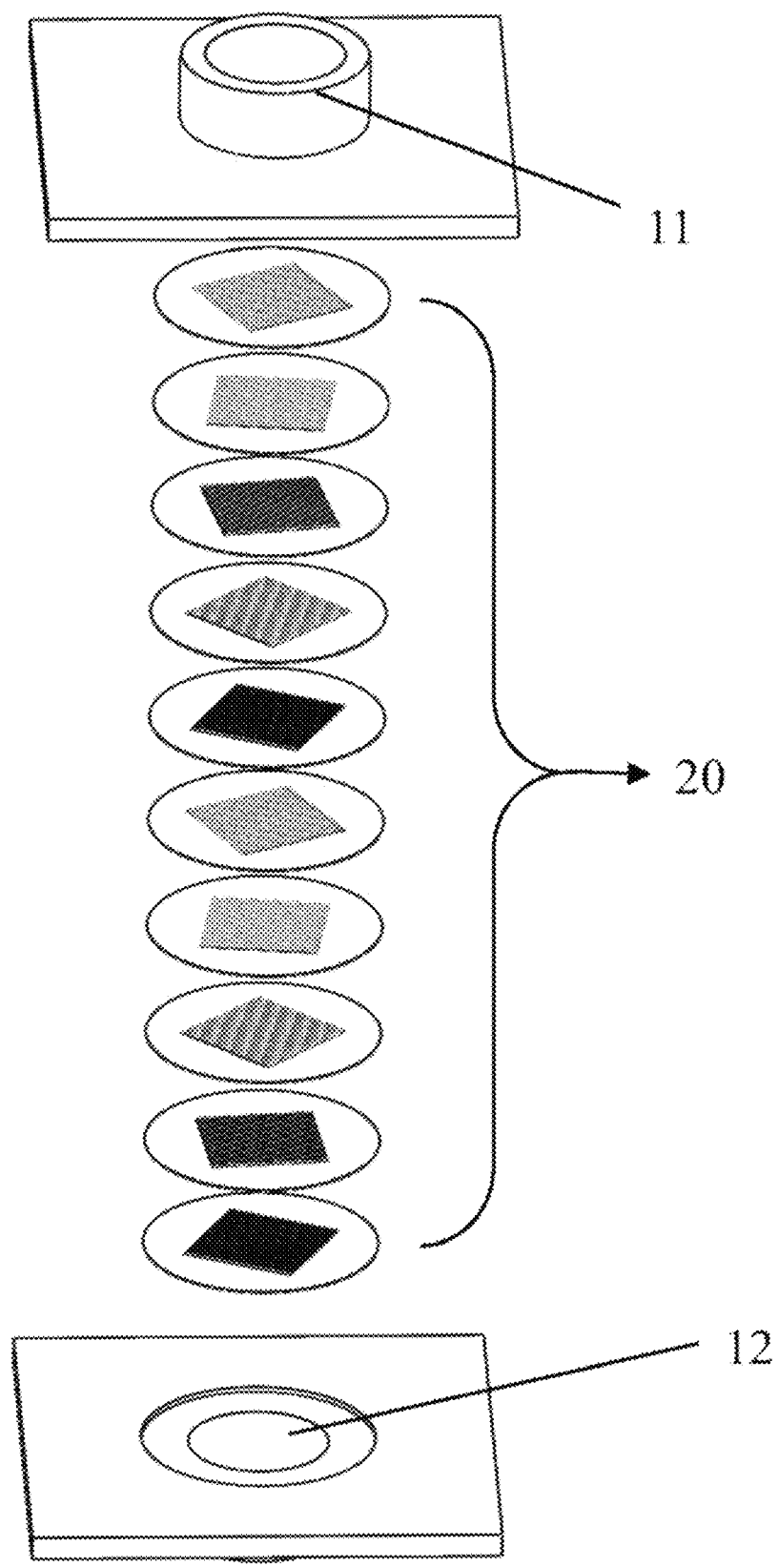
FIG. 3 is a first partial enlarged diagram of FIG. 2.
Figure 4:
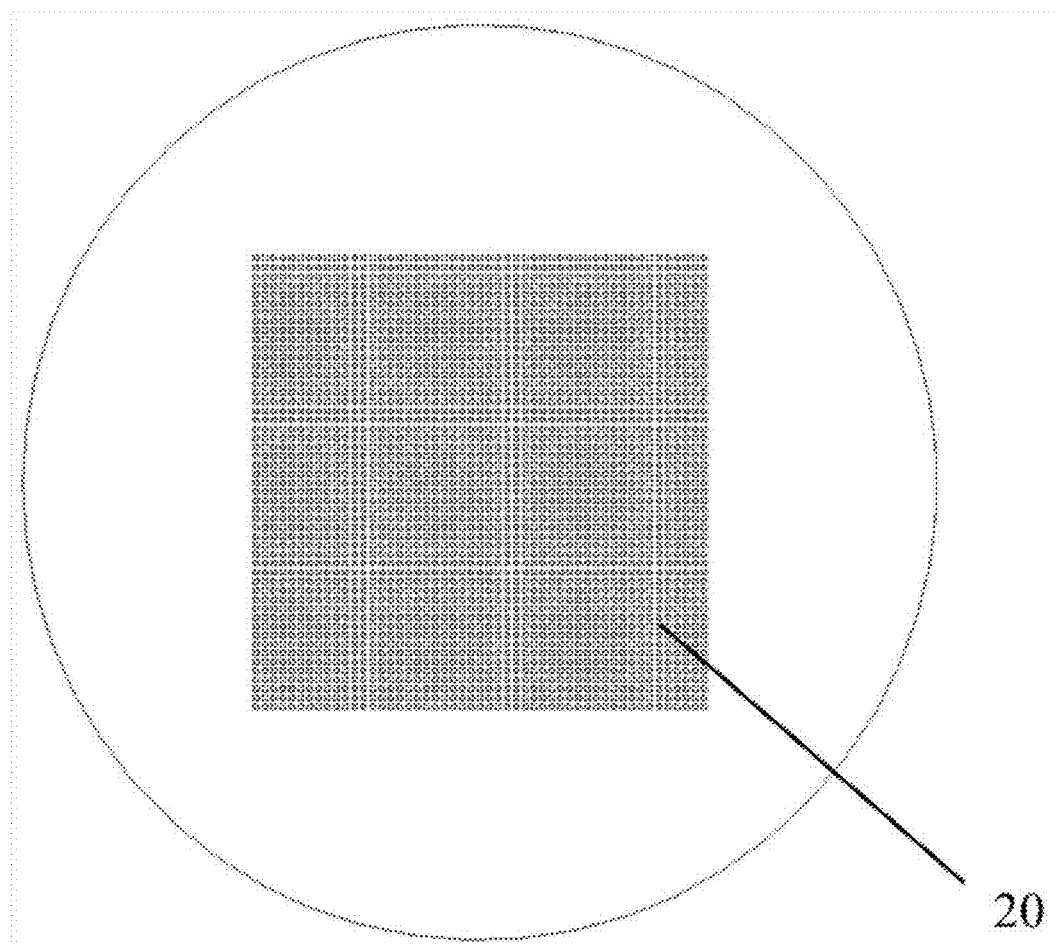
FIG. 4 is a second partial enlarged diagram of FIG. 2.

The following focuses on how to realize the staggered arrangement of the screen pores 22. As shown in FIGS. 2, 3 and 6, there is a rotation angle α at which an adjacent upper layer of the multi-channel mesh body 20 is rotated with respect to its lower layer of the multi-channel mesh body 20, taking the center of the adjacent layers of multi-channel mesh bodies 20 as the center of rotation, with the normal direction of the rotation plane perpendicular to the plane of the layers of the multi-channel mesh bodies 20. In the two adjacent layers of multi-channel mesh bodies 20, the lower layer of the multi-channel mesh body 20 is rotated 5 to 180° with respect to the upper layer of multi-channel mesh body 20, namely a ranges from 5 to 180°; preferably a ranges from 10 to 90°, further preferably a ranges from 30 to 60°. Further, each layer of the multi-channel mesh body 20 is rotated at the same angle in the same direction with respect to its upper layer of the multi-channel mesh body 20.

The parametric representation of the rotation angle of the plurality of multi-channel mesh bodies 20 is expressed as [0: m: n], wherein, 0 represents that taking the first layer of the multi-channel mesh body 20 as a reference, the angle of the first layer of the multi-channel mesh body 20 is 0°; m is a rotation angle of an (N+1)th layer of the multi-channel mesh body 20 with respect to an Nth layer of the multi-channel mesh body 20; n is a rotation angle of the last layer of the multi-channel mesh body 20 with respect to the first layer of multi-channel mesh body 20, and the number of the multi-channel mesh bodies 20 is (n/m)+1. When there are two layers of the multi-channel mesh bodies 20, the parametric representation of the rotation angle of the plurality of the multi-channel mesh bodies 20 is expressed as [0: m], that is, the second layer of the multi-channel mesh body 20 is rotated m° with respect to the first layer of the multi-channel mesh body 20.

For example, in one implementation, when the parametric representation of the rotation angle of the plurality of multi-channel mesh bodies 20 is expressed as [0:9:81], it represents that a layer of the multi-channel mesh body 20 is rotated 9° with respect to its upper layer of the multi-channel mesh body 20, and the number of the multi-channel mesh bodies 20 is 10. According to another implementation, when the parametric representation of the rotation angle of the plurality of the multi-channel mesh bodies 20 is expressed as [0:180], it represents that a layer of the multi-channel mesh body 20 is rotated 180° with respect to its upper layer of the multi-channel mesh body 20, and the number of the multi-channel mesh bodies 20 is 2.

The following focuses on the specific specifications of the mesh wires 23 and the screen pores 22.

The shape of the cross section of the screen pores 22 is selected from the square, rectangular, triangular, polygonal, circular, parallelogram, trapezoid, and combinations thereof. Herein, as shown in FIG. 6, the diameter D of the mesh wires 23 ranges from 10 μm to 500 μm, preferably 20 μm to 200 μm, further preferably 20 to 50 μm, more preferably 40 to 50 μm.

Herein, the thickness of the mesh wires 23 ranges from 10 μm to 500 μm, preferably 20 μm to 200 μm, further preferably 20 to 50 μm, more preferably 40 to 50 μm. The cross-sectional area of the screen pores ranges from 10 to 6000 μm², preferably 20 to 3000 μm², further preferably 700 to 3000 μm², more preferably 700 to 2000 μm². The space between two adjacent layers of the multi-channel mesh bodies 20 ranges from 0.1 to 10 mm, preferably 0.5 to 1.5 mm.

In order to specifically bind with the target object 3, the capturing layer comprises capturing material 21 that can specifically bind with the target object 3. In particular, the capturing material 21 is bonded to the mesh bodies by means of physical adsorption and/or chemical bonding. Preferably, the capturing material 21 is connected to the mesh bodies through Traut's reagent or a thiolate molecule with biotin-avidin. As shown in FIG. 5, the capturing material 21 can specifically bind with the target object 3 such as cells, bacteria, or biomolecules.

Herein, the capturing material 21 is a specific antibody or other type of specific recognition molecule for the target cells, bacteria or target molecules, for example, antibodies, phages, and aptamers, and the target molecule of the capturing material comprises, EpCAM, EphB4, EGFR, HER2, HER-2/neu, MUC-1, folate receptor, AFP, CEA, Cyfra21-1, TPA, TPS, NMP22, B2-MG, thyroglobulin, ferritin, CA19-9, CA125, CA50, CA72-4, CA242, CA15-3, SCC, LDH, NSE, PSA, ER, progesterone receptor, HCG β-hCG, prolactin, ACTH, calcitonin, DHEA-S, cortisol, aldosterone, uPA/PAI-1,5-hydroxytryptamine, 5-hydroxyindole acetic acid, HGH, FSH, LH, TSH, paraprotein, thymidine kinase, neopterin, SEA, protein S-100, M2-PK, chromogranin A, bone-specific alkaline phosphatase, deoxypyridinoline, CASA, epinephrine substances, catecholamines, homovanillic acid, epinephrine substances, vanillylmandelic acid, f-PSA, PCA3, AFP, placental alkaline phosphatase, calcitonin, gastrin, TSA, AFU, YGT, ALP, CA549, PAP, Bence-Jones protein, and various bacteria and other types of target objects.

The capturing material 21 is specifically determined according to the target object 3. The following table non-limitingly lists the target objects that can be used for enriching and screening with the device of the present disclosure and the associated disease types.

| Name of target object | Associated diseases of the captured target molecule |
|---|---|
| Alpha-fetoprotein (AFP) | liver cancer |
| Carcinoembryonic antigen (CEA) | breast cancer, pancreas cancer, bile duct/gallbladder cancer, lung cancer, cervical cancer, colorectal cancer, gastric cancer, renal cancer, liver cancer, bronchogenic cancer (adenocarcinoma, large cell cancer), thyroid cancer (medullary cancer), uterine cancer, ovarian cancer, bladder cancer |
| Cytokeratin-19-fragment | lung cancer, bladder cancer, bronchogenic cancer (oat cell carcinoma, squamous cell carcinoma, adenocarcinoma, large cell cancer) |
| Tissue-type plasminogen activator (TPA) | bladder cancer, renal cancer, bronchogenic cancer (oat cell carcinoma, adenocarcinoma), uterine cancer, lung cancer, cervical cancer |
| Human total protein S (TPS) | breast cancer, lung cancer, nasopharyngeal cancer |
| NMP22 (urine) | bladder cancer |
| Serumβ2-microglobulin (β2-MG) | lymphocytic/myelocytic leukemia |
| Thyroglobulin (TG) | thyroid cancer (papilloma, follicular tumor) |
| Ferritin | breast cancer |
| Epithelial cell adhesion molecule (EpCAM) | lung cancer, prostate cancer, small intestinal cancer, breast cancer, bladder cancer |
| EphB4 (ephrin type-B receptor 4) | breast cancer, colorectal cancer, head and neck cancer |
| Epidermal growth factor receptor (EGFR) | breast cancer, small intestinal cancer, gastric cancer |
| Human epidermal growth factor receptor 2 (HER2) | breast cancer, gastric cancer |
| Mucus protein 1 (MUC-1) | colorectal cancer, ovarian cancer, breast cancer, prostate cancer |
| Folate receptor (FR) | lung cancer |
| Carbohydrate antigen 19-9 (CA19-9) | bile duct/gallbladder cancer, colorectal cancer, gastric cancer, ovarian cancer, pancreatic cancer, uterine cancer |
| Carbohydrate antigen 125 (CA125) | pancreatic cancer, ovarian cancer (epithelial cancer, mucinous carcinoma), uterine cancer, cervical cancer |
| Cancer antigen 50 (CA50) | gastric cancer, pancreatic cancer, colorectal cancer |
| Carbohydrate antigen (CA72-4) | gastric cancer, ovarian cancer (mucinous carcinoma) |
| Cancer antigen 242 (CA242) | pancreatic cancer, rectal cancer, gastric cancer |
| Carbohydrate antigen (CA15-3) | breast cancer |
| Squamous cell carcinoma antigen (SCC) | cervical cancer, head and neck malignant tumor, esophageal cancer, bronchogenic cancer (squamous cell carcinoma), lung cancer |
| Lactate dehydrogenase (LDH) | testicular cancer (genital cell tumor, seminoma) |
| Neuron-specific enolase (NSE) | lung cancer, neuroendocrine tumor, pheochromocytoma, paraganglioma, bronchogenic cancer (oat cell carcinoma), testicular cancer (seminoma) |
| Prostate specific antigen (PSA) | prostate cancer |
| Estrogen receptor (ER) | breast cancer |
| Progesterone receptor (PR) | breast cancer |
| Human Chorionic gonadotropin (HCG) | testicular tumor, breast cancer, ovarian cancer |
| β-Human chorionic gonadotropin (β-HCG) | Choriocarcinoma, testicular cancer (genital cell tumor, seminoma) |
| Prolactin (PRL) | pituitary adenoma |
| Adrenocorticotrophic hormone (ACTH) | pituitary adenoma, bronchogenic cancer (oat cell carcinoma), lung cancer |
| Calcitonin (CT) | thyroid medullary carcinoma, bronchogenic cancer (oat cell carcinoma), lung cancer, breast cancer |
| Dehydroepiandrosterone sulfate (DHEA-S) | adrenocortical adenoma |
| Cortisol | adrenocortical adenoma |
| Aldosterone | adrenocortical adenoma |
| Urokinase-type plasminogen activator and plasminogen activator inhibitor type 1 (uPA/PAI-1 (Gewebe)) | breast cancer |
| 5-hydroxytryptamine (5-HT) | carcinoid |
| 5-hydroxyindole acetic acid (5-HIAA) | carcinoid |
| Human growth hormone (HGH) | pituitary adenoma |
| Follicle-stimulating hormone (FSH) | pituitary adenoma |
| Luteinizing hormone (LH) | pituitary adenoma |
| Thyroid stimulating hormone (TSH) | pituitary adenoma |
| Paraprotein | lymphocytic/myelocytic leukemia |
| Thymidine kinase | lymphocytic/myelocytic leukemia |
| Neopterin | lymphocytic/myelocytic leukemia |
| Thalassemia protein (SEA) | head and neck malignant tumor, esophageal cancer |
| Protein S-100 | melanoma |
| Pyruvate kinase-M2 (antigen) (M2-PK) | renal cancer |

-continued

| Name of target object | Associated diseases of the captured target molecule |
|---|---|
| ChromograninA (CGA) | neuroendocrine tumor |
| Bone-specific alkaline phosphatase (Ostase) | osteosarcoma, bone metastatic cancer |
| Deoxypyridinoline (urine) (DPD) | osteosarcoma, bone metastatic cancer |
| CASA (alpha-S1-casein, casoxin-D) | ovarian cancer (epithelial cancer) |
| Epinephrine substances (plasma) | pheochromocytoma, paraganglioma |
| Catecholamine (urine) (CA) | pheochromocytoma, paraganglioma |
| Homovanillic acid (urine) (HVA) | pheochromocytoma, paraganglioma |
| Epinephrine substances (urine) | pheochromocytoma, paraganglioma |
| Vanillylmandelic acid (urine) (VMA) | pheochromocytoma, paraganglioma |
| Free prostate specific antigen (f-PSA) | prostate cancer |
| Prostate cancer antigen3 (PCA3) (urine) | prostate cancer |
| Alpha-fetoprotein (AFP) | liver cancer, testicular cancer (genital cell tumor, seminoma) |
| Placental alkaline phosphatase | testicular cancer (seminoma) |
| Calcitonin (after giving pentagastrin) | thyroid cancer (medullary cancer) |
| Gastrin | gastrinoma |
| Trichostatin A (TSA) | lung cancer |
| α-L-fucosidase (AFU) | liver cancer |
| γ-glutamyltranspeptidase (γGT) | liver cancer |
| Alkaline phosphatase (ALP) | liver cancer |
| Carbohydrate antigen 549 (CA549) | breast cancer |
| Prostatic acid phosphatase (PAP) | prostate cancer |
| Bence-Jones protein (BJP) | myeloma |
| *Escherichia Coli* | hemorrhagic diarrhea, complicated with hemolytic uremic syndrome and thrombotic thrombocytopenic purpura |
| *Staphylococcus aureus* | pustulosis |
| *Bacillus tetani* | tetanus |
| *Bacillus tuberculosis* | tuberculosis |

In order to improve the capture rate and increase the specificity of the multi-channel mesh bodies 20, the present disclosure may also provide different capturing materials 21 on two layers of multi-channel mesh bodies 20 in the enriching and screening mechanism, or different capturing materials 21 on three layers of multi-channel mesh bodies 20. Preferably, each layer of multi-channel mesh body 20 has a different capturing material 21.

Herein, in the enriching and screening mechanism, the capturing materials 21 on at least two layers of multi-channel mesh bodies 20 specifically bind with the same kind of target cell, bacteria, or biomolecule 3; preferably, the capturing materials 21 on at least three layers of multi-channel mesh bodies 20 specifically bind with the same kind of target cell, bacteria, or biomolecule 3; further preferably, the capturing materials 21 on at least four layers of the multi-channel mesh bodies 20 specifically bind with the same kind of target cell, bacteria, or biomolecule 3; most preferably, the capturing material 21 on each layer of the multi-channel mesh bodies 20 specifically binds with the same kind of target cell, bacteria, or biomolecule 3.

According to one implementation, there are 5 multi-channel mesh bodies 20, and the capturing material 21 on each layer of the multi-channel mesh bodies 20 is different, the capturing materials 21 on the five layers are antibodies specifically binding with EphB4, EGFR, HER2, CEA and ferritin, respectively, and these five capturing materials 21 all specifically bind with the same target cell, namely breast cancer tumor cells.

Herein, in order to screen different kinds of target cells, bacteria, or biomolecules 3 at one time, in the plurality of multi-channel mesh bodies 20, the capturing material 21 on at least one layer of multi-channel mesh body 20 specifically binds with a kind of target cell, bacteria, or biomolecule 3, and the capturing material 21 on at least another one layer of multi-channel mesh body 20 specifically binds with another kind of target cell, bacteria, or biomolecule 3. Preferably, the capturing material 21 on each layer of multi-channel mesh bodies 20 specifically binds with different target cells, bacteria, or biomolecules 3.

According to another implementation, there are 10 multi-channel mesh bodies 20, and the capturing material 21 on each layer of the multi-channel mesh bodies 20 is different, the target molecules 3 to which the capturing materials 21 on the ten layers specifically bind are respectively listed as follows: HER-2/neu (serum, tissue)—breast cancer; folate receptor (FR)—lung cancer; NMP22 (urine)—bladder cancer; prolactin (PRL)—pituitary adenoma; DHEA-S-adrenocortical tumor; 5-hydroxytryptamine (5-HT)—carcinoid; protein S-100—melanoma; M2—PK-renal cancer; chromogranin A (CGA)—neuroendocrine tumor; PAP—prostatic cancer. 10 different capturing materials 21 specifically bind to 10 different target molecules or to the surfaces of different target cells (when the target molecules are expressed on the outer surface of the target cells).

In the following, the present disclosure is further explained in detail combining with specific embodiments. The raw materials not specifically stated in the embodiments are all commercially available. The operation without special mention of temperature is carried out at room temperature. Operation methods and conditions that are not specifically described can use well-known or conventional methods and conditions in the art.

Embodiment 1

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wire 23 has a thickness of 22 μm and a diameter of 22 μm, the cross-section of the screen pores 22 was square-shaped, and the cross-sectional area of the screen pores 22 was 54×54 μm$^2$.

The capturing material on each layer of the multi-channel mesh bodies 20 was EpCAM antibody, and the method for connecting the capturing material to the multi-channel mesh bodies 20 comprises the following steps:
(1) 4.6 μl Traut's reagent solution (0.2 mg/ml), 5 μl EPCAM antibody (Cat #ab32392, Abcam), 40.4 μl PBS-EDTA (2.5 mmol, pH 8.0) were mixed and incubated at room temperature for one hour;
(2) The solution incubated in Step (1) was dropped onto the multi-channel mesh bodies 20, and incubated at room temperature for one hour;
(3) 1 ml of PBS solution was added into the multi-channel mesh bodies 20 to rinse, and the remaining solution was removed;
(4) Step (3) was repeated;
(5) 1 ml of 2% BSA solution (BSA with 2% of the total mass of BSA solution and PBS solution with 98% of the total mass of the BSA solution) was added to the multi-channel mesh bodies 20, and then incubated at room temperature for 30 minutes;
(6) The multi-channel mesh bodies 20 were installed and fixed in the cavity of the main body.

Applying the enriching and screening mechanism prepared above to capture circulating tumor cells comprises the following steps:
(1) 0.5 mL of cell suspension containing 10 lung cancer cells was injected into the enriching and screening mechanism;
(2) 0.5 mL of cell suspension was flowed through the inlet 11 of the enriching and screening mechanism, the cell suspension was flowed through 10 layers of multi-channel mesh bodies 20 at a speed of $7.8 \times 10^{-5}$ m/s, to cause lung cancer cells binding to the enriching and screening mechanism;
(3) 0.5 ml of PBS solution was added to wash the multi-channel mesh bodies 20 at a rate of 100 microliters per minute to remove unbound sundries, cells or molecules;
(4) The multi-channel mesh bodies 20 were detached, and the detached multi-channel mesh bodies 20 were placed in 0.5 mL of eluent (pancreatin accounts for 0.25% of the total mass of the eluent, 1 mM EDTA and the remaining PBS solution), incubated at 37° C. for 2 minutes, then shaken for 10 seconds to separate lung cancer cells from the enriching and screening mechanism;
(5) 0.5 mL of neutralization solution (fetal bovine serum) was added, the multi-channel mesh bodies 20 were taken out, centrifuged at a speed of 300 g for 5 minutes, the supernatant was removed, and the cell precipitate was re-suspended in PBS or cell culture medium and counted, and the number of entrapped lung cancer cells was 8.

Embodiment 2

It is basically the same as Embodiment 1, and differs in that: the parameter of the rotation angle of the plurality of multi-channel mesh bodies 20 was [0:9:81], that is, a lower layer of the multi-channel mesh body 20 was rotated 9° with respect to an upper layer of the multi-channel mesh body 20.

The number of entrapped lung cancer cells was 5.

Embodiment 3

It is basically the same as Embodiment 1, and differs in that: there were 7 layers of multi-channel mesh bodies 20, and the parameter of the rotation angle of the plurality of multi-channel mesh bodies 20 was [0:60:240], that is, a lower layer of the multi-channel mesh body 20 was rotated 60° with respect to an upper layer of the multi-channel mesh body 20.

The number of entrapped lung cancer cells was 4.

Embodiment 4

It is basically the same as Embodiment 1, and differs in that: there were 7 layers of multi-channel mesh bodies 20, and the parameter of the rotation angle of the plurality of multi-channel mesh bodies 20 was [0:60:240], that is, a lower layer of the multi-channel mesh body 20 was rotated 60° with respect to an upper layer of the multi-channel mesh body 20. The mesh wire 23 had a thickness of 44 μm and a diameter of 44 μm.

The number of entrapped lung cancer cells was 7.

Embodiment 5

It is basically the same as Embodiment 1, and differs in that: there were 7 layers of multi-channel mesh bodies 20, and the parameter of the rotation angle of the plurality of multi-channel mesh bodies 20 was [0:60:240], that is, a lower layer of the multi-channel mesh body 20 was rotated 60° with respect to an upper layer of the multi-channel mesh body 20. The cross-sectional area of the screen pores 22 was 27×27 μm$^2$.

The number of entrapped lung cancer cells was 6.

Embodiment 6

It is basically the same as Embodiment 1, and differs in that: there were 7 layers of multi-channel mesh bodies 20, and the parameter of the rotation angle of the plurality of multi-channel mesh bodies 20 was [0:60:240], that is, a lower layer of the multi-channel mesh body 20 was rotated 60° with respect to an upper layer of the multi-channel mesh body 20. The mesh wire 23 had a thickness of 44 μm and a diameter of 44 μm, and the cross-sectional area of the screen pores 22 was 27×27 μm$^2$.

The number of entrapped lung cancer cells was 10.

Embodiment 7

It is basically the same as Embodiment 1, and differs in that: the mesh wire 23 had a thickness of 44 μm and a diameter of 44 μm, and the cross-sectional area of the screen pores 22 was 27×27 μm$^2$.

The number of entrapped lung cancer cells was 10.

Embodiment 8

It is basically the same as Embodiment 7, and differs in that: the circumscribed circle radius of the screen pores 22 having a square cross-section was 27 μm.

The number of entrapped lung cancer cells was 10.

Embodiment 9

It is basically the same as Embodiment 7, and differs in that: the screen pores 22 had a triangular cross-section with a circumscribed circle radius of 27 μm.

The number of entrapped lung cancer cells was 10.

Embodiment 10

It is basically the same as Embodiment 7, and differs in that: the screen pores 22 had a hexagonal cross-section with a circumscribed circle radius of 27 μm.

The number of entrapped lung cancer cells was 10.

Comparative Example 1

There were a total of 10 multi-channel mesh bodies 20, the 10 multi-channel mesh bodies 20 were arranged in parallel and a rotation angle there between was 0°, the mesh wires 23 had a thickness of 44 μm and a diameter of 44 μm, and the cross-sectional area of the screen pores 22 was 27×27 μm$^2$. The capturing material 21 on each layer of multi-channel mesh body 20 was EpCAM antibody.

The circulating tumor cells were captured according to the method of Embodiment 1, and the number of entrapped lung cancer cells in this contrast was 4.

Embodiment 11

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wires 23 had a thickness of 44 μm and a diameter of 44 μm, the cross-section of the screen pores 22 was square-shaped, and the cross-sectional area of the screen pores 22 was 27×27 μm$^2$.

The capturing material connected to the first multi-channel mesh body 20 was EpCAM antibody, the capturing material connected to the second multi-channel mesh body 20 was EphB4 antibody, the capturing material connected to the third multi-channel mesh body 20 was EGFR antibody, the capturing material connected to the fourth multi-channel mesh body 20 was HER2 antibody, the capturing material connected to the fifth multi-channel mesh body 20 was MUC-1 antibody, the capturing material connected to the sixth multi-channel mesh body 20 was CEA antibody, the capturing material connected to the seventh multi-channel mesh body 20 was ferritin antibody, the capturing material connected to the eighth multi-channel mesh body 20 was CA15-3 antibody, the capturing material connected to the ninth multi-channel mesh body 20 was ER antibody, and the capturing material connected to the tenth multi-channel mesh body 20 was progesterone receptor antibody. The method for connecting the respective capturing materials to the multi-channel mesh bodies 20 is basically the same as Embodiment 1.

Applying the enriching and screening mechanism prepared above to capture circulating tumor cells comprises the following steps:

(1) 0.5 mL of cell suspension containing 10 breast cancer cells was injected into the enriching and screening mechanism;

(2) 0.5 mL of cell suspension was flowed through the inlet 11 of the enriching and screening mechanism, the cell suspension was flowed through 10 layers of multi-channel mesh bodies 20 at a speed of 7.8×10−5 m/s, to cause breast cancer cells binding to the enriching and screening mechanism;

(3) 0.5 ml of PBS solution was added to wash the multi-channel mesh bodies 20 at a rate of 100 microliters per minute to remove unbound sundries, cells or molecules;

(4) The multi-channel mesh bodies 20 were detached, and the detached multi-channel mesh bodies 20 were placed in 0.5 mL of eluent (pancreatin accounts for 0.25% of the total mass of the eluent, 1 mM EDTA and the remaining PBS solution), incubated at 37° C. for 2 minutes, then shaken for 10 seconds to separate breast cancer cells from the enriching and screening mechanism;

(5) 0.5 mL of neutralization solution (fetal bovine serum) was added, the multi-channel mesh bodies 20 were taken out, centrifuged at a speed of 300 g for 5 minutes, the supernatant was removed, and the cell precipitate was re-suspended in PBS or cell culture medium and counted, and the number of entrapped breast cancer cells was 10.

Embodiment 12

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wires 23 had a thickness of 44 μm and a diameter of 44 μm, the cross-section of the screen pores 22 was square-shaped, and the cross-sectional area of the screen pores 22 was 27×27 μm$^2$.

The capturing material connected to the first multi-channel mesh body 20 was EphB4 antibody, the capturing material connected to the second multi-channel mesh body 20 was folate receptor antibody, the capturing material connected to the third multi-channel mesh body 20 was AFP antibody, the capturing material connected to the fourth multi-channel mesh body 20 was NMP22 antibody, the capturing material connected to the fifth multi-channel mesh body 20 was B2-MG antibody, the capturing material connected to the sixth multi-channel mesh body 20 was thyroglobulin antibody, the capturing material connected to the seventh multi-channel mesh body 20 was PSA antibody, the capturing material connected to the eighth multi-channel mesh body 20 was prolactin antibody, the capturing material connected to the ninth multi-channel mesh body 20 was protein S-100 antibody, and the capturing material connected to the tenth multi-channel mesh body 20 was Bence-Jones protein antibody. The method for connecting the capturing materials to the multi-channel mesh bodies 20 is basically the same as Embodiment 1.

Applying the enriching and screening mechanism prepared above to capture circulating tumor cells comprises the following steps:

(1) 5 mL of cell suspension respectively containing 10 breast cancer cells, 10 liver cancer cells, 10 bladder cancer cells, 10 lymphocytic/myelocytic leukemia cells, 10 thyroid cancer cells, 10 prostate cancer cells, 10 pituitary tumor cells, 10 melanoma cells, 10 myeloma cells was injected into the enriching and screening mechanism;
(2) The cell suspension was flowed through the inlet 11 of the enriching and screening mechanism at a speed of 7.8×105 m/s, the cell suspension was flowed through 10 layers of multi-channel mesh bodies 20 in order to cause breast cancer cells binding to the enriching and screening mechanism;
(3) 0.5 ml of PBS solution was added to wash the multi-channel mesh bodies 20 at a rate of 100 microliters per minute to remove unbound sundries, cells or molecules;
(4) The 10 multi-channel mesh bodies 20 were detached, and each of the detached multi-channel mesh bodies 20 was respectively placed in 0.5 mL of eluent (pancreatin accounts for 0.25% of the total mass of the eluent, 1 mM EDTA and the remaining PBS solution), incubated at 37° C. for 2 minutes, then shaken for 10 seconds to separate lung cancer cells from the enriching and screening mechanism; 0.5 mL of neutralization solution (fetal bovine serum) was added, the multi-channel mesh bodies 20 were taken out, centrifuged at a speed of 300 g for 5 minutes, the supernatant was removed, and the cell precipitate was re-suspended in PBS cell culture medium.
(5) The target cells on each of multi-channel mesh bodies 20 were collected and counted, the number of entrapped breast cancer cells was 3, the number of entrapped lung cancer cells was 4, the number of entrapped liver cancer cells was 7, the number of entrapped bladder cancer cells was 6, the number of entrapped lymphocytic/myelocytic leukemia cells was 4, the number of entrapped thyroid cancer cells was 6, the number of entrapped prostate cancer cells was 6, the number of entrapped pituitary tumor cells was 4, the number of entrapped melanoma cells was 5, and the number of entrapped myeloma cells was 7.

Embodiment 13

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wires 23 had a thickness of 22 μm and a diameter of 22 μm, the cross-section of the screen pores 22 was square-shaped, and the cross-sectional area of the screen pores 22 was 54×54 μm².

The capturing material on each layer of the multi-channel mesh bodies 20 was phages, and the capturing material was connected to the multi-channel mesh bodies 20 to form phage-capturing screens. The preparation of the phage-capturing screens comprises the following steps:
  5 μl Traut's reagent solution (7 μM), 10 μl *Escherichia coli* recombinant phage (provided by Rapifage) ($10^{11}$ cfu/mL), 75 μl PBS-EDTA (2.5 mmol, pH 8.0) were mixed and incubated at room temperature for one hour;
(2) The solution incubated in Step (1) was dropped onto the multi-channel mesh bodies 20, and incubated at room temperature for one hour, to form phage-capturing screens;
(3) 1 ml of PBS solution was added into the multi-channel mesh bodies 20 to rinse, and the remaining solution was removed;
(4) Step (3) was repeated;
(5) 1 ml of 2% BSA solution (BSA with 2% of the total mass of BSA solution and PBS solution with 98% of the total mass of the BSA solution) was added to the phage-capturing screens, and then incubated at room temperature for 30 minutes;
(6) The phage-capturing screen was installed and fixed within the cavity of the main body. Applying the above enriching and screening mechanism to capture *Escherichia coli* (O157: H7, provided by Beijing 301 Hospital), comprises the following steps:
(1) 0.5 mL of suspension containing *Escherichia coli* (concentration: 10 cfu/mL), was injected into the enriching and screening mechanism;
(2) 0.5 mL of *Escherichia coli* suspension was flowed through the inlet 11 of the enriching and screening mechanism, and through 10 layers of phage-capturing screens at a speed of $7.8 \times 10^{-5}$ m/s, to cause *Escherichia coli* binding to the phage-capturing screens;
(3) 0.5 ml of PBS solution was added to wash the phage-capturing screens at a rate of 100 microliters per minute to remove unbound sundries, cells or molecules;
(4) The fluorescence signal of the phage-capturing screens was recorded and analyzed using a fluorescence microscope with a CCD image sensor, and according to the formula: capture rate=100%*(the number of bacteria in the stock solution−the number of bacteria in the rinse solution)/the number of bacteria in the stock solution, the *Escherichia coli* capture rate was calculated to be 99.1%.

Embodiment 14

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wires 23 had a thickness of 22 μm and a diameter of 22 μm, the cross-section of the screen pores 22 was square-shaped, and the cross-sectional area of the screen pores 22 was 54×54 μm².

The capturing material on each layer of the multi-channel mesh bodies 20 was goat anti-*Escherichia coli* 0157: H7 antibody (provided by KPL), and the capturing material was connected to the multi-channel mesh bodies 20 to form antibody-capturing screens. The preparation of the antibody-capturing screens comprises the following steps:
(1) 5 μl Traut's reagent solution (7 μM), 50 μg/mL antibody, 75 μl PBS-EDTA (2.5 mmol, pH 8.0) were mixed and incubated at room temperature for one hour.
(2) The solution incubated in Step (1) was dropped onto the multi-channel mesh bodies 20, and incubated at room temperature for one hour, to form antibody-capturing screens.
(3) 1 ml of PBS solution was added into the antibody-capturing screens to rinse, and the remaining solution was removed.
(4) Step (3) was repeated.
(5) 1 ml of 2% BSA solution (BSA with 2% of the total mass of BSA solution and PBS solution with 98% of the total mass of the BSA solution) was added to the antibody-capturing screens, and then incubated at room temperature for 30 minutes.

(6) The antibody-capturing screen was installed and fixed within the cavity of the main body.

Applying the above enriching and screening mechanism to capture *Escherichia coli* (O157: H7, provided by Beijing 301 Hospital), comprises the following steps:

(1) The *Escherichia coli* strain was added to acridine orange (Sinopharm Chemical Reagent Co., Ltd.), and the final concentration of acridine orange was 5 μg/mL. 0.5 mL of *Escherichia coli* suspension with a concentration of 10 cfu/mL was injected into the enriching and screening mechanism;

(2) 0.5 mL of *Escherichia coli* suspension was flowed through the inlet 11 of the enriching and screening mechanism, and through 10 layers of antibody-capturing screens at a speed of $7.8 \times 10^{-5}$ m/s, to cause *Escherichia coli* binding to the antibody-capturing screens;

(3) 0.5 ml of PBS solution was added to wash the antibody-capturing screens at a rate of 100 microliters per minute to remove unbound sundries, cells or molecules;

(4) The fluorescence signal of the antibody-capturing screens was recorded and analyzed using a fluorescence microscope with a CCD image sensor, and according to the formula: capture rate=100%*(the number of bacteria in the stock solution−the number of bacteria in the rinse solution)/the number of bacteria in the stock solution, the *Escherichia coli* capture rate was calculated to be 98.2%.

Embodiment 15

In an enriching and screening mechanism, the parameter of the rotation angle of the plurality of multi-channel mesh bodies 20 was [0:36:324], that is, a lower layer of the multi-channel mesh body 20 was rotated 36° with respect to an upper layer of the multi-channel mesh body 20, and there were a total of 10 multi-channel mesh bodies 20.

The gap between two adjacent layers of multi-channel mesh bodies 20 was 1 mm, the mesh wires 23 had a thickness of 22 μm and a diameter of 22 μm, the cross-section of the screen pores 22 was square-shaped, and the cross-sectional area of the screen pores 22 was 54×54 μm².

The capturing material on each layer of the multi-channel mesh bodies 20 was aptamer (sequence: 5'-biotin-TTAGCAAAGTAGCGTGCACTT-3', provided by Sangon Biotech Co., Ltd.), and the capturing material was connected to the multi-channel mesh bodies 20 through biotin-avidin, to form aptamer-capturing screens. The preparation of the phage-capturing screens comprises the following steps:

(1) The surface of the multi-channel mesh bodies 20 was modified using reagents, to obtain a biotin-modified multi-channel mesh bodies;

(2) A 10 mM streptomycin solution was prepared, and adjusted to pH 8.0, the biotin-modified multi-channel mesh bodies were washed with pH 7.4 PBS buffer for 3-5 times, 200 μL of the prepared streptomycin solution was added, and the system was shaked overnight at 37° C.;

(3) 200 μL of 0.5 M mercaptoethanol (MCH) with pH 8.0 was added to the streptomycin-coated multi-channel mesh bodies, and reacted in a shaker at 37° C. for 6 hours to block uncoupled groups, to improve the specificity of aptamer-screening. The mercaptoethanol not bound to the capturing screen was washed with PBS buffer with pH 7.4 to obtain affinity screens coupled with streptomycin.

(4) 0.6 μmol/L aptamer was added to the affinity screens coupled with streptomycin, mixed evenly, and incubated for 15 min to obtain the aptamer-capturing screens;

(5) The aptamer-capturing screen was washed with Tris-HCL for 3 times, and installed and fixed within the cavity of the main body.

Applying the above enriching and screening mechanism to capture *Escherichia coli* (O157: H7, provided by Beijing 301 Hospital), comprises the following steps:

(1) The *Escherichia coli* strain was added to acridine orange to obtain an *Escherichia coli* suspension, and the final concentration of acridine orange was 5 μg/mL. 0.5 mL of *Escherichia coli* suspension with a concentration of 10 cfu/mL was injected into the enriching and screening mechanism;

(2) 0.5 mL of *Escherichia coli* suspension was flowed through the inlet 11 of the enriching and screening mechanism, and through 10 layers of aptamer-capturing screens at a speed of $7.8 \times 105$ m/s, to cause *Escherichia coli* binding to the aptamer-capturing screens;

(3) 0.5 ml of PBS solution was added to wash the aptamer-capturing screens at a rate of 100 microliters per minute to remove unbound sundries, cells or molecules;

(4) The fluorescence signal of the antibody-capturing screens was recorded and analyzed using a fluorescence microscope with a CCD image sensor, and according to the formula: capture rate=100%*(the number of bacteria in the stock solution−the number of bacteria in the rinse solution)/the number of bacteria in the stock solution, the *Escherichia coli* capture rate was calculated to be 98.7%.

As above described, the present disclosure is explained according to the purpose thereof, but the present disclosure is not limited to the above-mentioned embodiments and implement methods. Various variations and implementations can be made by the practitioners of the relative technical fields within the technical concept of the present disclosure.

What is claimed is:

1. An enriching and screening apparatus, comprising:
a main body comprising an inlet, an outlet, and a cavity located between the inlet and the outlet; and
a plurality of multi-channel mesh bodies fixed within the cavity, each multi-channel mesh body of the plurality of multi-channel mesh bodies comprising:
a mesh body formed by intersecting mesh wire, the intersecting mesh wire including a first plurality of mesh wires extending in a first direction that intersect with a second plurality of mesh wires extending in a second direction that is transverse to the first direction;
a plurality of screen pores, the plurality of screen pores defined by openings located between the first plurality of mesh wires and the second plurality of mesh wires; and
a capturing layer bonded to the mesh body, the capturing layer including capturing materials configured to bind with a target object, wherein the capturing materials are selected from antibodies, phages, or aptamers;
wherein the plurality of multi-channel mesh bodies are arranged in a vertical direction within the cavity such that at least a first multi-channel mesh body of the plurality of multi-channel mesh bodies is positioned in a first horizontal plane and a second multi-channel mesh body of the plurality of multi-channel mesh bodies is positioned in a second horizontal plane that is below the first horizontal plane, and a space between the first horizontal plane and the second horizontal plane is 0.1-10 mm;

wherein screen pores of the first multi-channel mesh body are at least partially staggered with respect to screen pores of the second multi-channel mesh body when the plurality of multi-channel mesh bodies are arranged in the vertical direction within the cavity;

wherein the screen pores of the first multi-channel mesh body are at least partially staggered with respect to the screen pores of the second multi-channel mesh body as a function of the first multi-channel mesh body being oriented at an angle with respect to the second multi-channel mesh body, and the angle is between 30-60°;

wherein a thickness of the intersecting mesh wire ranges from 10 μm to 500 μm;

wherein capturing materials of a capturing layer of the first multi-channel mesh body are the same as capturing materials of a capturing layer of the second multi-channel mesh body.

2. The enriching and screening apparatus according to claim 1, wherein the thickness ranges from 20 μm to 200 μm.

3. The enriching and screening apparatus according to claim 1, wherein the openings located between the first plurality of mesh wires and the second plurality of mesh wires have from 700 to 2000 μm².

4. The enriching and screening apparatus according to claim 1, wherein a number of the plurality of multi-channel mesh bodies ranges from 2 to 30.

5. The enriching and screening apparatus according to claim 1, wherein a number of the plurality of multi-channel mesh bodies ranges from 3 to 15.

6. The enriching and screening apparatus according to claim 1, wherein a cross-section of the openings is square, rectangular, triangular, polygonal, circular, parallelogram, or trapezoid.

* * * * *